United States Patent
Lal et al.

(10) Patent No.: US 7,166,755 B2
(45) Date of Patent: Jan. 23, 2007

(54) SYNTHESIS OF PENTAFLUOROSULFANYLNAPHTHALENE

(75) Inventors: Gauri Sankar Lal, Whitehall, PA (US); Kristen Elaine Minnich, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 69 days.

(21) Appl. No.: 10/954,719

(22) Filed: Sep. 30, 2004

(65) Prior Publication Data

US 2006/0069285 A1    Mar. 30, 2006

(51) Int. Cl.
*C07C 19/08*    (2006.01)
(52) U.S. Cl. ........................................ 570/130
(58) Field of Classification Search ................ 570/101, 570/123, 127, 129, 130, 131, 161, 162, 176, 570/186, 187, 188
See application file for complete search history.

(56) References Cited

U.S. PATENT DOCUMENTS

| 6,479,645 | B1 | 11/2002 | Lal et al. |
| 2003/0216476 | A1 | 11/2003 | Kleemann |

FOREIGN PATENT DOCUMENTS

| EP | 1 533 297 A1 | 5/2005 |
| WO | WO 2004/011422 | 2/2004 |
| WO | WO 2004/0011422 A1 | 2/2004 |

OTHER PUBLICATIONS

Peer Kirsch, et al, Liquid Crystals Based on Hypervalent Sulfur Fluorides: . . . , Angew. Chem. Int. Ed. 1999, 38, No. 13/14, p. 1989-1991.
Wm. A. Sheppard, Arylsulfur Pentafluorides, J. Am. Chem. Soc. 1962, 84, p. 3064-3072.
Roy D. Bowden, et al, A New Method for the Synthesis of Aromatic . . . , Tetrahedron, 2000, 56, p. 3399-3408.
R.W. Winter, et al; "Synthesis of SF5-benzene (SF5C6H5) by the SF5-halide method"; Journal of Fluorine Chemistry, vol. 125, No. 4; Apr. 2004; pp. 549-552.
F.W. Hoover, et al; "Synthesis and chemistry of ethynylsulphur pentrafluoride"; Journal of Organic Chemistry, vol. 29, No. 12; Dec. 1964; pp. 3567-3570.

*Primary Examiner*—Thurman K. Page
*Assistant Examiner*—Karl Puttlitz
(74) *Attorney, Agent, or Firm*—Geoffrey L. Chase

(57) ABSTRACT

This invention relates to 2-pentafluorosulfanylnapthalene, substituted derivatives thereof and to a process for producing naphthalene carrying an $SF_5$ group. A 3-step process is employed wherein 1,4-dihydronaphthalene is reacted with pentafluorosulfanyl halide. Next the resulting 3-halo-2-pentafluorosulfanylnaphthalene or derivative is converted to 2-pentafluorosulfanyl-1,4-dihydronaphthalene or derivative by treatment with a base and subsequently transformed into pentafluorosulfanylnaphthalene by removing hydrogen atoms.

18 Claims, No Drawings

SYNTHESIS OF PENTAFLUOROSULFANYLNAPHTHALENE

BACKGROUND OF THE INVENTION

Fluorine incorporation in organic compounds is known to have a profound influence on the physical and chemical properties such as biological activity and electronegativity. A trifluoromethyl group has been employed as an effective means for introducing fluorine into such compounds. An alternative to trifluoromethyl incorporation has been the addition of sulfur pentafluoride. The high electronegativity value of the $SF_5$ group, 3.62 on the Pauling scale, and greater electron withdrawing ability suggest that it affords an attractive alternative to the trifluoromethyl group ("$CF_3$") found in many commercial products such as dye-stuffs, anesthetics, fluoropolymers, electronic components, and chemotherapeutic agents.

Pentafluorosulfanyl derivatives of aromatic compounds have been produced but the study of these compounds has been limited because of the lack of good synthetic routes. $SF_5$ addition to fused aromatic compounds is unknown.

Representative articles and patents illustrating addition of a sulfur pentafluoride group to organic compounds are as follows:

U.S. Pat. No. 6,479,645 discloses the silyl sulfurpentafluoride and substituted ethyne compounds useful as a precursor for a variety of organic compounds. Substituted silyl acetylenic compounds are reacted with an $SF_5$ halide under condition to form an vinyl pentafluorosulfuanyl intermediate followed by addition of base. $SF_5Br$ addition to trimethylsilylacetylene resulted in the product, pentafluorosulfuranyl-2-trimethyl silylethyne.

US 2003/0216476 A1 discloses the preparation of pentafluorosulfanylbenzoylguanidines. These compounds were found to be suitable as antiarrythmic agents and for treatment of angina pectoris.

JP 2004/059452A, discloses the preparation of N-ribobenzimidazole bearing an $SF_5$ group. This compound was found to be an effective anti-viral and anti-cancer agent.

Kirsch, et. al in *Agnew. Chem. Int. Ed.* 1999, 38, 13, 1989 reported in the article, *Liquid Crystals Based Upon Hypervalent Sulfur Fluorides: Pentafluorosulfuranyl as Polar Terminal Group*, disclose the application of aryl sulfurpentafluorides as liquid crystals and demonstrated an improved electro-optical property of the —$SF_5$ group over the —$CF_3$ group. Pentafluorosulfuranylbenzene derivatives were produced by direct fluorination of deactivated aromatic disulfides.

Sheppard and co-workers, *J. Am. Chem. Soc.* 1962, 84, 3064 disclose in an article *Arylsulfur Pentafluorides*, the reaction of aryl disulfides with silver difluoride to obtain phenyl sulfurpentafluoride and nitrophenyl sulfurpentafluoride in ~30% yield.

Bowden et al, Tetrahedron, 2000, 56, 3399, in an article *A New Method for the Synthesis of Aromatic Sulfurpentafluorides and Studies of the Stability of the Sulfurpentafluoride Group in common Synthetic Transformations*, disclose the reaction of aryl disulfides with $F_2$ in the presence of $CH_3CN$ to produce nitrophenylsulfurpentafluorides. The nitrophenylsulfurpentafluorides then were converted to aminophenyl sulfurpentafluorides, biphenylsulfurpentafluoride, acetamidophenyl sulfurpentafluoride, and the like.

Hoover et al, *J. Am. Chem. Soc.* 1964, 3567 in an article entitled, *Synthesis And Chemistry Of Ethynylsulfur Pentafluoride* disclosed a procedure to phenyl sulfurpentafluoride and dimethylphenyl sulfurpentafluoride involving a Diels-Alder cycloaddition reaction of butadiene and 2,3-dimethylbutadiene respectively with ethynyl sulfurpentafluoride.

WO 011422A1 discloses the preparation of pentafluorosulfanylbenzene via the reaction of $SF_5Cl$ with 4,5-dichloro-1-cyclohexene and pentasulfanylalkenes by reacting $SF_5Cl$ with an alkene.

BRIEF SUMMARY OF THE INVENTION

This invention relates to pentafluorosulfanyl derivatives of fused aromatic compounds and particularly to the compounds, 2-pentafluorosulfanylnapthalene and substituted derivatives thereof, and to a process for producing naphthalene carrying an $SF_5$ group. A 3-step process is preferred wherein 1,4-dihydronaphthalene is reacted with $SF_5Br$ in the presence of $B(Et)_3$. Next the resulting 3-bromo-2-pentafluorosulfanylnaphthalene is converted to 2-pentafluorosulfanyl-1,4-dihydronaphthalene by treatment with a base and subsequently transformed into pentafluorsulfanylnaphthalene by oxidation with 2,3-dichloro-5,6-dicyano-benzoquinone (DDQ.)

Significant advantages are achieved by the process and the synthesis of the fused aromatic compounds incorporating an $SF_5$ group, e.g., 2-pentafluorosulfanylnapthalene and its derivatives, and they include:

an ability to incorporate an $SF_5$ group onto a fused aromatic compound, e.g., naphthalene or derivative and thus provide for unique properties in a fused aromatic;

an ability to generate fluorinated organics having suitability for producing liquid crystal components;

an ability to produce materials having electro-optical properties;

an ability to produce fused aromatic compounds incorporating an $SF_5$ group via a route which may lead to viable medicinal and agrochemical products; and, an ability to use a 3 step process for the production of fused aromatic compounds having an $SF_5$ group.

DETAILED DESCRIPTION OF THE INVENTION

As pointed out in the background, $SF_5$ incorporation into aromatic compounds has been limited because of a want of acceptable synthetic methods. $SF_5$ addition to fused aromatic compounds had not been an option for the organic chemist as $SF_5$ does not add directly. Routes employing direct fluorination of aromatic disulfides have not afforded a method for producing pentafluorosulfanyl derivatives of fused aromatic compounds either.

A process has been developed not only where $SF_5$ is incorporated into a fused aromatic, e.g., naphthalene but also where the bonding in the aromatic ring is conjugated in relationship to the $SF_5$ group. Thus, the compound exhibits unique electronic activity not only because of the $SF_5$ incorporation but also because of the conjugated bond structure.

In the first step of the process, 1,4-dihydronaphthalene is contacted with an $SF_5$ halide such as $SF_5Br$ or $SF_5Cl$ under conditions for effecting addition of the $SF_5$ group in the 2-position. This is necessary in the reaction scheme in order to achieve proper bond placement in subsequent process steps. The reaction is preferably carried out in the presence of triethylborane $B(Et)_3$ acting as a catalyst. Other catalysts may be employed and these include free radical generators, benzoyl peroxide and azo compounds and ultra violet light.

In the second step, assuming SF$_5$Br was the reactant in the first step, bromine is removed from the 3-bromo-2-pentafluorosulfanyinaphthalene produced in the first step. Dehydrobromination is effected by treatment of the brominated compound with a base under conditions for removing bromine. The base reactant suited for dehalogenation, e.g., dehydrobromination, may include alkali or alkaline earth metal hydroxides, alkoxides, amides, amines, metal alkyl derivatives. However, because the process requires removal of halide from the 3-position, the use of SF$_5$Br is preferred as a reactant in the first step because of ease of bromine removal. Should SF$_5$Cl have been used as the reactant, dehydrochlorination of the compound, 3-chloro-2-pentafluorosulfanylnaphthalene, would have been required and removal of chlorine is difficult in this kind of reaction.

In the third step, the 2-pentafluorosulfanyl-1,4-dihydronaphthalene or derivative formed in step 2 is oxidized, i.e., 2 hydrogen atoms are removed and the fused product, 2-pentafluorosulfanylnapthalene or derivative, formed. Oxidation or dehydrogenation of 2-pentafluorosulfanyl-1,4-dihydronaphthalene can be achieved by reaction with 2,3-dichloro-5,6-dicyano-benzoquinone (DDQ.) On oxidation with DDQ, conjugated bonding is achieved in the aromatic ring in relation to the SF$_5$ group. As such, the conjugated bonding, coupled with the SF$_5$ functionality provides for desired electronic characteristics. Other reagents which can effect dehydrogenation include benzoquinone and other oxidants such as O$_2$ in the presence of activated carbon, nitric acid, nitrites of alkali metals, salts of Ce, Cu, Bi, Mn, and Zr. Metals such as Pt, Pd should also be suitable.

The process steps for producing pentafluorosulfanyl naphthalenes and derivatives wherein the SF$_5$ group is in the 2-position are outlined below.

Step 1

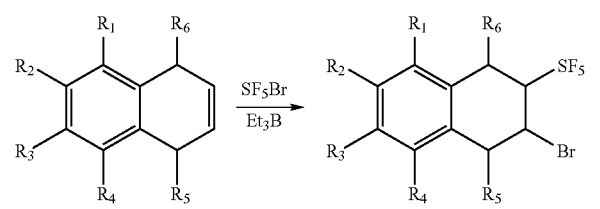

Step 2

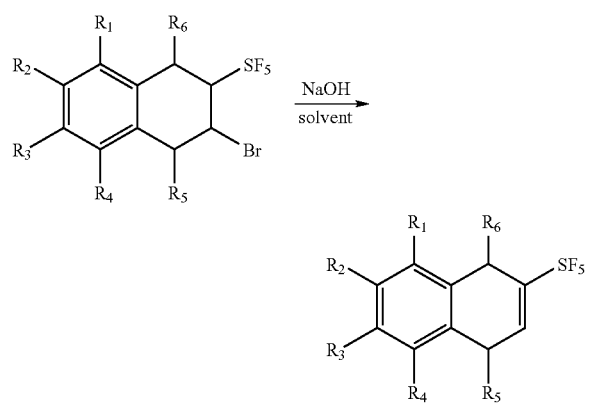

Step 3

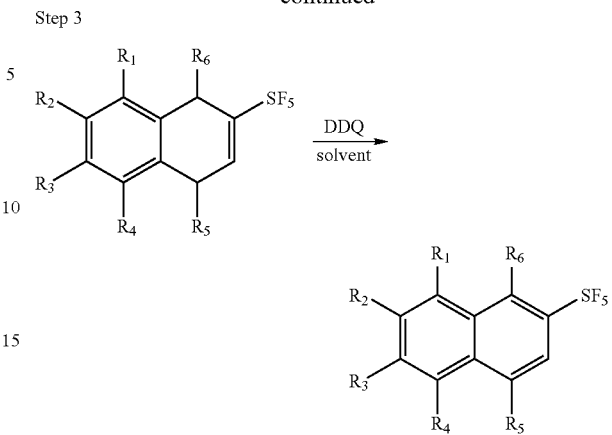

wherein $R_{1-4}$ are H, $C_{1-6}$ alkyl, substituted $C_{1-6}$alkyl, aryl or substituted aryl; O, S, and N hetero compounds, —COOR$_7$ where R$_7$ is $C_{1-6}$ alky, —COR, where R$_8$ is $C_{1-6}$ alkyl or halogen, i.e., F, Cl, Br, and I; boron esters, $(R_9)_3$B where R$_9$ is $C_{1-6}$ alkyl, and R$_5$ and R$_6$ are H. Typically, only one or two substituents of $R_{1-4}$ are other than hydrogen may be appended to the ring. For example, one or two of R$_1$ to R$_4$ may be C$_1$ alkyl. In cases where substitution is desired, substitution on the R$_3$ is position is preferred, such as F, Cl, Br or I.

Substituted derivatives may be formed by forming a substituted 1,4-dihydronapthalene prior to contact and reaction with the SF$_5$ halide. Alternatively, substituents may be incorporated subsequent to formation of the desired compound. A problem with the second approach is that reaction may take place in the 1, 3, or 4 position of the fused aromatic Representative named pentafluorosulfanyinapthalene derivatives are represented by the formula:

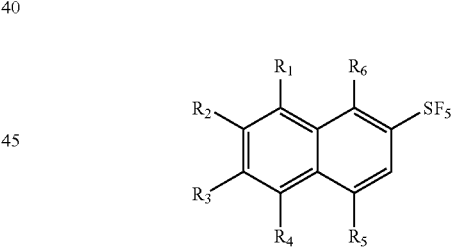

are as follows: 6-bromo-2-pentafluorosulfanylnaphthalene, 6-chloro-2-pentafluorosulfanylnaphthalene, 6-fluoro-2-pentafluorosulfanylnaphthalene, 6-iodo-2-pentafluorosulfanyl-naphthalene, 6-methyl-2-pentafluorosulfanylnaphthalene, 6-propyl-2-pentafluorosulfanyinaphthalene, 6-pentyl-2-pentafluorosulfanylnaphthalene, 6-cyclohexyl-2-pentafluorosulfanylnaphthalene, 6-(4-propylcyclohexyl)-2-pentafluorosulfanylnaphthalene, 6-carboethoxy-2-pentafluorosulfanylnaphthalene, 6-trimethylsilyl-2-pentafluorosulfanyinaphthalene, 6-trimethoxyborane-2-pentafluorosulfanylnaphthalene, and 6-trimethylborane-2-pentafluorosulfanylnaphthalene.

In the above series of reactions solvents may be used as necessary and these include hydrocarbons, fluorocarbons, nitriles, ethers, halocarbons, and other solvents, which will not react with reactants such as the base. Reaction temperatures typically range from −78° C. to the boiling point of solvent. Reaction products may be purified by standard methods including distillation and chromatography.

The following examples are provided to illustrate various embodiments and comparisons and are not intended to restrict the scope of the invention.

EXAMPLE 1

Preparation of Step 1

Preparation of 3-bromo-2-pentafluorosulfanylnaphthalene 1,4 Dihydronaphthalene (2 g, 15.3 mmol), pentane (100 mL), potassium fluoride (0.3 g) and triethylborane (1.6 mL, 1M in hexanes) were charged to 300 cc ss Parr reactor. The solution was cooled and degassed. $SF_5Br$ (18 mmol) was condensed into the reactor at −50° C. The reaction was stirred for 1 hour then the cooling bath was removed and stirring was continued one hour. The solution was poured into cold sodium bicarbonate, phases were separated and pentane layer dried over magnesium sulfate.

Step 2

Preparation of the Product pentafluorsulfanyl-1,4-dihydronaphthalene

Powdered sodium hydroxide (5 equivalents) was added to the pentane solution and stirred at room temperature. The reaction was monitored by GC. When the reaction was complete, base was removed by filtration and pentane was removed by rotary evaporation.

Step 3

Preparation of Pentafluorosulfanylnaphthalene

Toluene and dichlorodicyanobenzoquinone (2 equivalents) were added to the product of step 2 and heated to 65° C. The reaction was monitored by GC. When the reaction was complete pentane was added. Resulting solids were removed by filtration. Color was removed by filtering through silica. The crude product was isolated by removing the solvent using rotary evaporation.

The product was purified by sublimation. Residual solvent and naphthalene by-product were removed under vacuum at room temperature. The product sublimed at 35° C./220 mTorr and was identified by mass spectrometry, $^1H$ and $^{19}F$ NMR.

What is claimed is:

1. A compound represented by the formula:

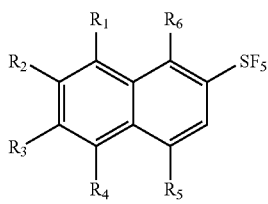

wherein $R_{1-4}$ are H, $C_{1-6}$ alkyl, substituted $C_{1-6}$alkyl, aryl or substituted aryl; O, S, and N hetero compounds, —$COOR_7$ where $R_7$ is $C_{1-6}$ alkyl, —$COR_8$ where $R_8$ is $C_{1-6}$ alkyl; F, Cl, Br, I; boron $C_{1-6}$ alkyl ester, $(R_9)_3B$ where $R_9$ is $C_{1-6}$ alkyl, and $R_5$ and $R_6$ are H.

2. The compound of claim 1 wherein $R_{1-4}$ is H.

3. The compound of claim 1 wherein $R_3$ is $C_{1-6}$ alkyl and $R_1$, $R_2$, and $R_4$ are H.

4. The compound of claim 1 wherein $R_3$ is —$COOR_7$ where $R_7$ is $C_{1-6}$ alkyl and $R_1$, $R_2$, and $R_4$ are H.

5. The compound of claim 1 wherein $R_3$ is —$COR_8$ where $R_8$ is $C_{1-6}$ alkyl and $R_1$, $R_2$, and $R_4$ are H.

6. The compound of claim 1 wherein $R_3$ is a boron $C_{1-6}$ alkyl ester and $R_1$, $R_2$, and $R_4$ are H.

7. The compound of claim 1 wherein $R_3$ is, $(R_9)_3B$ where $R_9$ is $C_{1-6}$ alkyl and $R_1$, $R_2$, and $R_4$ are H.

8. The compound of claim 1 wherein $R_3$ is halogen and $R_1$, $R_2$, and $R_4$ are H.

9. The compound of claim 8 wherein $R_3$ is F, Cl, Br, or I.

10. A compound selected from the group consisting of 6-bromo-2-pentafluorosulfanylnaphthalene, 6-chloro-2-pentafluorosulfanylnaphthalene, 6-fluoro-2-pentafluorosulfanylnaphthalene, 6-iodo-2-pentafluorosulfanylnaphthalene, 6-methyl-2-pentafluorosulfanylnaphthalene, 6-propyl-2-pentafluorosulfanyinaphthalene, 6-pentyl-2-pentafluorosulfanyinaphthalene, 6-cyclohexyl-2-pentafluorosulfanylnaphthalene, 6-(4-propylcyclohexyl)-2-pentafluorosulfanyinaphthalene, 6-carboethoxy-2-pentafluorosulfanylnaphthalene, 6-trimethylsilyl-2-pentafluorosulfanylnaphthalene, 6-trimethoxyborane-2-pentafluorosulfanylnaphthalene, and 6-trimethylborane-2-pentafluorosulfanylnaphthalene.

11. A process for producing a compound of the formula A:

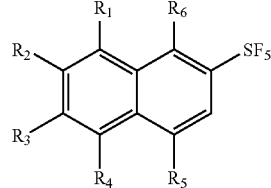

wherein $R_{1-4}$ are H, $C_{1-6}$ alkyl, substituted $C_{1-6}$ alkyl, aryl or substituted aryl; O, S, and N hetero compounds, —$COOR_7$ where $R_7$ is $C_{1-6}$ alkyl, —$COR_8$ where $R_8$ is $C_{1-6}$ alkyl; F, Cl. Br, and I; boron $C_{1-6}$ esters, $(R_9)_3B$ where $R_9$ is $C_{1-6}$ alkyl, and $R_5$ and $R_6$ are H which comprises the steps:

(a) contacting a reactant of the formula B:

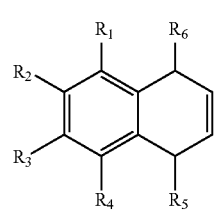

wherein $R_{1-4}$ are H, $C_{1-6}$ alkyl, substituted $C_{1-6}$ alkyl, aryl or substituted aryl; O, S, and N hetero compounds, —$COOR_7$ where $R_7$ is $C_{1-6}$ alkyl, —$COR_8$ where $R_8$ is $C_{1-6}$ alkyl; F, Cl. Br, and I; boron $C_{1-6}$ esters, $(R_9)_3B$ where $R_9$ is $C_{1-6}$ alkyl, and $R_5$ and $R_5$ are H with an $SF_5$ bromide to form compound C:

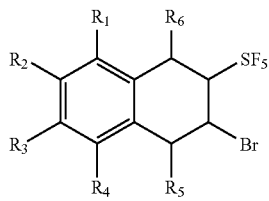

C wherein $R_{1-4}$ are H, $C_{1-6}$ alkyl, substituted $C_{1-6}$ alkyl, aryl or substituted aryl; O, S, and N hetero compounds, —$COOR_7$ where $R_7$ is $C_{1-6}$ alkyl, —$COR_8$ where $R_8$ is $C_{1-6}$ alkyl; F, Cl, Br, and I; boron $C_{1-6}$ esters, $(R_9)_3B$ where $R_9$ is $C_{1-6}$ alkyl, and $R_5$ and $R_6$ are H;

(b) dehydrobrominating compound C to form compound D having the formula:

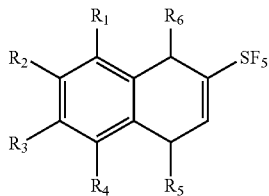

D and then;

(c) removing hydrogen from compound D under conditions for producing compound A.

12. The process of claim 11 wherein at least one of $R_1$, $R_2$ and $R_4$ are H.

13. The process of claim 11 wherein $R_3$ is $C_{1-6}$ alkyl.

14. A process for producing 2-pentafluorosulfanylnaphthalene which comprises the steps:

(a) contacting 1,4-dihydronaphthalene with $SF_5Br$ in the presence of a catalyst to form 3-bromo-2-pentafluorosulfanylnaphthalene;

(b) removing bromine from the compound 3-bromo-2-pentafluorosulfanylnaphthalene formed in step (a) thus forming pentafluorosulfanyl-1,4-dihydronaphthalene; and, (c) removing two hydrogen atoms from the thus formed pentafluorosulfanyl-1,4-dihydronaphthalene in step (b) to produce 2-pentafluorosulfanylnaphthalene.

15. The process of claim 14 wherein the catalyst is triethylborane.

16. The process of claim 14 wherein bromine is removed by treatment with a base.

17. The process of claim 16 wherein the base is NaOH.

18. The process of claim 14 wherein two hydrogen atoms are removed in step (c) by reaction with dichlorodicyanobenzoquinone.

* * * * *